United States Patent
Kodama et al.

(10) Patent No.: US 9,913,607 B2
(45) Date of Patent: Mar. 13, 2018

(54) COLLISION AVOIDANCE SYSTEM AND COLLISION AVOIDANCE METHOD

(71) Applicant: The Yokohama Rubber Co., LTD., Minato-ku, Tokyo (JP)

(72) Inventors: Yuji Kodama, Hiratsuka (JP); Koji Nakatani, Hiratsuka (JP)

(73) Assignee: The Yokohama Rubber Co., LTD. (JP)

( * ) Notice: Subject to any disclaimer, the term of this patent is extended or adjusted under 35 U.S.C. 154(b) by 0 days.

(21) Appl. No.: 15/533,972

(22) PCT Filed: Dec. 26, 2014

(86) PCT No.: PCT/JP2014/084577
§ 371 (c)(1),
(2) Date: Jun. 7, 2017

(87) PCT Pub. No.: WO2016/103468
PCT Pub. Date: Jun. 30, 2016

(65) Prior Publication Data
US 2017/0325732 A1    Nov. 16, 2017

(51) Int. Cl.
*A61B 5/18*    (2006.01)
*G08G 1/16*    (2006.01)
*B60Q 1/52*    (2006.01)
*B60Q 1/26*    (2006.01)

(52) U.S. Cl.
CPC .............. *A61B 5/18* (2013.01); *B60Q 1/26* (2013.01); *B60Q 1/52* (2013.01); *B60Q 1/525* (2013.01); *G08G 1/162* (2013.01); *G08G 1/163* (2013.01)

(58) Field of Classification Search
None
See application file for complete search history.

(56) References Cited

U.S. PATENT DOCUMENTS

| | | | |
|---|---|---|---|
| 5,990,795 A * | 11/1999 | Miller | G08B 21/06 180/272 |
| 2009/0237257 A1 | 9/2009 | Yamada et al. | |
| 2011/0115617 A1* | 5/2011 | Bennett | B60Q 1/50 340/439 |
| 2012/0095646 A1* | 4/2012 | Ghazarian | G01S 19/17 701/36 |

(Continued)

FOREIGN PATENT DOCUMENTS

| | | |
|---|---|---|
| JP | S63-270240 | 11/1988 |
| JP | 3599426 | 12/2004 |

(Continued)

OTHER PUBLICATIONS

International Search Report for International Application No. PCT/JP2014/084577 Mar. 31, 2015, 6 pages, Japan, pages.

*Primary Examiner* — Laura Nguyen
(74) *Attorney, Agent, or Firm* — Thorpe North & Western (57) ABSTRACT

A driver state detection unit detects a state of the driver of a host vehicle. For example, a drowsing state of the driver is detected. An outward warning device performs an outward warning operation pertaining to a warning directed at another vehicle traveling in the vicinity of the host vehicle. Then, an inward warning device performs an inward warning operation pertaining to a warning directed at the driver of the host vehicle.

17 Claims, 8 Drawing Sheets

(56) References Cited

U.S. PATENT DOCUMENTS

| | | | | |
|---|---|---|---|---|
| 2013/0069773 A1* | 3/2013 | Li | ............... | B60K 28/02 |
| | | | | 340/426.1 |
| 2013/0297387 A1* | 11/2013 | Michael | ............... | G08G 1/0112 |
| | | | | 705/13 |
| 2015/0088397 A1* | 3/2015 | Burton | ............... | A61B 5/18 |
| | | | | 701/70 |
| 2015/0319411 A1* | 11/2015 | Kasmir | ............... | G08B 13/19684 |
| | | | | 348/143 |
| 2016/0052391 A1* | 2/2016 | Walsh | ............... | B60K 28/066 |
| | | | | 340/575 |
| 2016/0121791 A1* | 5/2016 | Shimizu | ............... | B60Q 1/525 |
| | | | | 340/435 |

FOREIGN PATENT DOCUMENTS

| | | |
|---|---|---|
| JP | 2005-190082 | 7/2005 |
| JP | 2009-223752 | 10/2009 |
| JP | 2011-057134 | 3/2011 |
| JP | 2011-128966 | 6/2011 |
| JP | 2013-182521 | 9/2013 |

\* cited by examiner

COLLISION AVOIDANCE SYSTEM AND COLLISION AVOIDANCE METHOD

TECHNICAL FIELD

The present technology relates to a collision avoidance system and a collision avoidance method.

BACKGROUND ART

It is dangerous to fall asleep at the wheel. Techniques to detect such a state are known. Japanese Unexamined Patent Application Publication No. 2011-128966A discloses a device that obtains feature points from a captured image of a driver's face and determines the sleepiness of the driver. Japanese Unexamined Patent Application Publication No. 2009-223752A discloses a device that calculates a degree of risk from the eye opening time and eye closing time of a driver and gives an alarm to the driver when the degree exceeds a threshold.

SUMMARY

If a vehicle being operated by a driver in a drowsy state approaches another vehicle, these vehicles may collide with each other. To avoid such a collision, a warning may be made to the driver driving in a drowsy state at appropriate timing.

The present technology provides a collision avoidance system and a collision avoidance method capable of increasing the likelihood of avoiding a collision between a vehicle being operated by a driver in a drowsy state and another vehicle.

A collision avoidance system according to an aspect of the present technology includes: a driver state detection unit configured to detect a state of a driver of a host vehicle; an outward warning device configured to perform an outward warning operation pertaining to a warning directed at another vehicle traveling in a vicinity of the host vehicle; an inward warning device configured to perform an inward warning operation pertaining to a warning directed at the driver of the host vehicle; and a control unit configured to control the outward warning device and the inward warning device on the basis of the state of the driver detected by the driver state detection unit. The control unit is configured to cause the outward warning device and the inward warning device to perform the outward warning operation and then performs the inward warning operation on the basis of the state of the driver.

The collision avoidance system may further include a distance measurement unit configured to measure a distance between the host vehicle and the other vehicle. Upon the distance measured by the distance measurement unit being within a predetermined range, the control unit may cause the outward warning device and the inward warning device to perform the outward warning operation and the inward warning operation.

Preferably, the other vehicle includes a following vehicle traveling behind the host vehicle.

Preferably, the driver state detection unit detects a drowsing state of the driver.

The driver state detection unit may include a brainwave sensor configured to detect brainwaves of the driver and detect the drowsing state of the driver on the basis of the brainwaves of the driver.

The driver state detection unit may include an imaging unit configured to detect an image of the driver and detect the drowsing state of the driver on the basis of the image of the driver.

The control unit may cause the outward warning operation to be performed and then, after a predetermined time elapses, cause the inward warning operation to be performed.

Preferably, the outward warning operation includes at least one of displaying a predetermined display directed at the other vehicle or emitting a predetermined sound toward the other vehicle.

The outward warning operation may include transmitting, to the other vehicle, a signal for activating another warning device provided in the other vehicle.

A collision avoidance method according to an aspect of the present technology includes the steps of: detecting a state of a driver of a host vehicle; performing an outward warning operation pertaining to a warning directed at another vehicle traveling in a vicinity of the host vehicle; and performing an inward warning operation pertaining to a warning directed at the driver of the host vehicle. The outward warning operation is performed and then the inward warning operation is performed on the basis of the state of the driver.

According to the collision avoidance system and the collision avoidance method of the present technology, when a determination is made that the host vehicle is being operated by a driver in a drowsy state, a warning is made to the other vehicle first, and then a warning is made to the driver of the host vehicle, thereby increasing the likelihood of avoiding a collision between the traveling vehicle and the other vehicle.

DETAILED DESCRIPTION

Embodiments of the present technology are described in detail below with reference to the drawings. However, the present technology is not limited by the embodiments. Furthermore, constituents of the embodiments include elements that may be easily replaced by those skilled in the art or that are substantially identical to the constituents of the embodiments. In addition, some of the constituents may not be used in some cases.

First Embodiment

Figure 1:
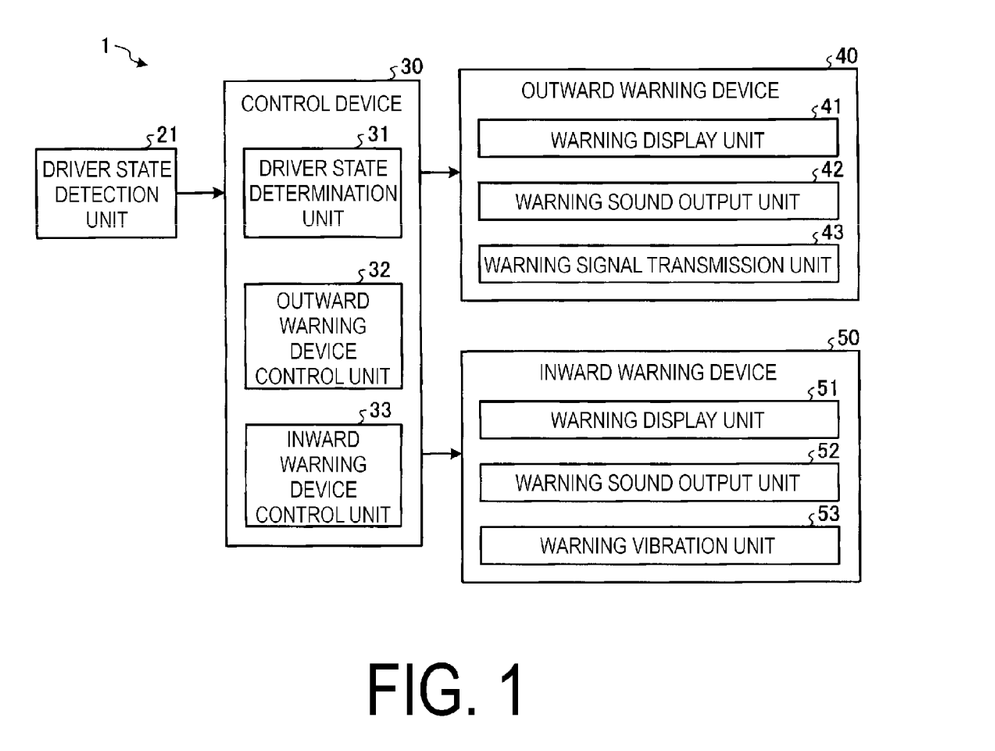
FIG. 1 is a function block diagram of a collision avoidance system according to a first embodiment.

FIG. 1 is a function block diagram of a collision avoidance system according to a first embodiment. As illustrated in FIG. 1, the collision avoidance system 1 according to the present embodiment is provided in a vehicle, and includes a driver state detection unit 21, a control device 30, an outward warning device 40, and an inward warning device 50.

The driver state detection unit 21 detects a state of the driver of a host vehicle. The driver state detection unit 21 detects, for example, a drowsing state of the driver.

The driver state detection unit 21 may include a brainwave sensor detecting brainwaves of the driver and detect the drowsing state of the driver on the basis of the brainwaves of the driver. The drowsing state of the driver may be detected on the basis of at least one of the theta wave or alpha wave of the brainwaves. Note that the brainwaves are a sum of electrical changes of the neuronal population existing below the scalp and skull, the changes being detected with electrodes placed on the scalp or skull.

The driver state detection unit 21 may further include a myoelectric sensor acquiring an electromyogram of the driver and detect the drowsing state of the driver on the basis of the brainwaves and electromyogram of the driver. For example, the drowsing state of the driver may be detected on the basis of the electromyogram and the theta wave and alpha wave of the brainwaves. Note that the electromyogram shows a sum of electrical changes caused by contractions of muscles.

The driver state detection unit 21 may include an imaging unit detecting an image of the driver and detect the drowsing state of the driver on the basis of the image of the driver. For example, the driver state detection unit 21 may capture an image of the driver's face, and analyzes the image to determine whether the driver is in a drowsing state. More specifically, when the eye closing time of the driver is longer than the eye opening time, the driver state detection unit 21 can determine that the driver is in a drowsing state.

The driver state detection unit 21 may include a biological optical measurement device measuring hemodynamic changes of the driver's brain and detect the drowsing state of the driver on the basis of the hemodynamic changes of the driver's brain. For example, the drowsing state of the driver may be detected with the biological optical measurement device disclosed in Japanese Patent No. 3599426.

The control device 30 includes a driver state determination unit 31, an outward warning device control unit 32, and an inward warning device control unit 33.

The driver state determination unit 31 determines a state of the driver on the basis of a detection result from the driver state detection unit 21. When the detection result from the driver state detection unit 21 is outside a predetermined range, for example, the driver state determination unit 31 determines that the driver is in a drowsing state.

The outward warning device control unit 32 causes the outward warning device 40 to perform a warning operation pertaining to a warning directed at another vehicle traveling in the vicinity of the host vehicle. The inward warning device control unit 33 causes the inward warning device 50 to perform a warning operation pertaining to a warning directed at the driver of the host vehicle.

The outward warning device 40 performs the warning operation pertaining to a warning directed at the other vehicle traveling in the vicinity of the host vehicle. The outward warning device 40 includes a warning display unit 41, a warning sound output unit 42, and a warning signal transmission unit 43.

The warning display unit 41 makes a warning by lighting a lamp, displaying an image, or the like, for example. Here, the lamp is not limited to a lamp originally provided in the vehicle to satisfy traffic regulations. In addition to displaying an image or lighting a lamp, flashing a lamp may be carried out (for example, flashing brake lamps). The display of an image is carried out by displaying a predetermined message on a display device using known LEDs, a liquid crystal display, or the like, for example.

The warning sound output unit 42 makes a warning by outputting a warning sound. The warning sound includes synthesized voice.

The warning signal transmission unit 43 wirelessly transmits, to another vehicle such as a following vehicle, a warning signal for causing another warning device provided in the other vehicle to operate.

The vehicle that has received the warning signal from the warning signal transmission unit 43 causes the warning device provided therein to operate so as to make a warning to the driver thereof.

The inward warning device 50 performs the warning operation pertaining to a warning directed at the driver of the host vehicle. The inward warning device 50 includes a warning display unit 51, a warning sound output unit 52, and a warning vibration unit 53.

The warning display unit 51 makes a warning by lighting a lamp, displaying an image, or the like, for example. The display of the image is carried out by displaying a predetermined message on a display device using known LEDs, a liquid crystal display, or the like, for example. When the host vehicle is provided with a navigation device, the image may be displayed on a liquid crystal display of the navigation device.

The warning sound output unit 52 makes a warning by outputting a warning sound. The warning sound includes synthesized voice.

The warning vibration unit 53 makes a warning by vibrating equipment in the host vehicle. For example, the warning is made to the driver by partially vibrating the steering wheel gripped by the driver.

Figure 2:
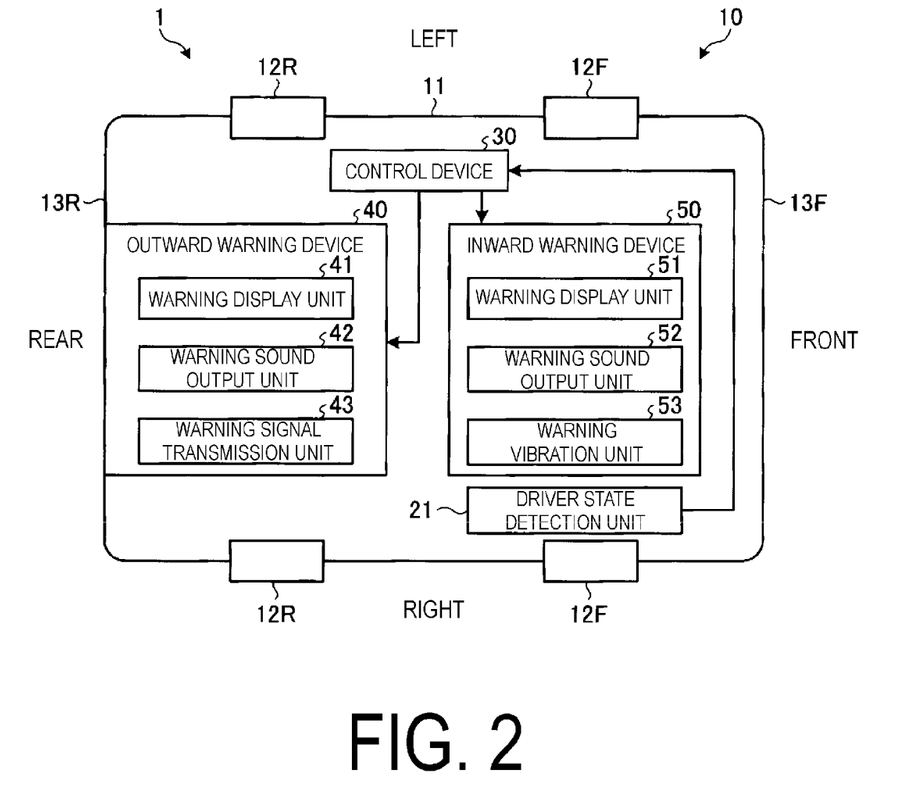
FIG. 2 is a schematic diagram of an example vehicle provided with the collision avoidance system according to the first embodiment.

FIG. 2 is a schematic diagram of an example vehicle provided with the collision avoidance system according to the present embodiment. As illustrated in FIG. 2, the host vehicle 10 is a four-wheeled vehicle in the present embodiment. The host vehicle 10 has two front wheels 12F and two rear wheels 12R. The host vehicle 10 has a driver cab that a driver occupies. Note that the host vehicle 10 may be a vehicle other than four-wheeled vehicles.

Figure 3:
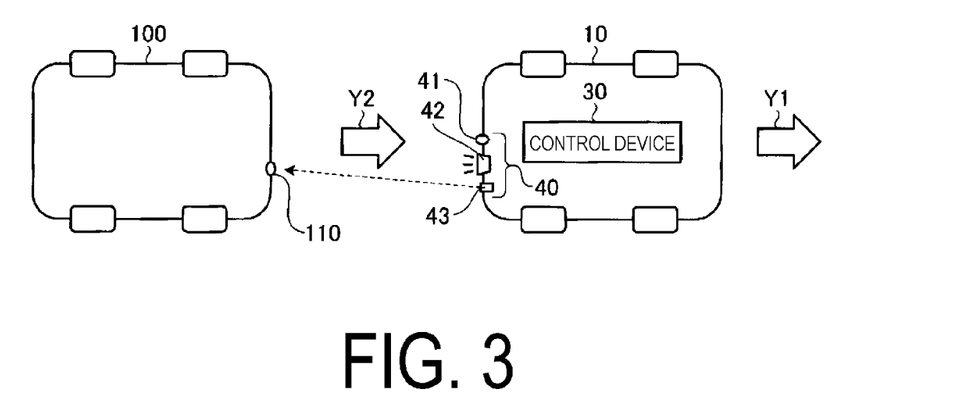
FIG. 3 is a schematic diagram of operations performed by the collision avoidance system illustrated in FIGS. 1 and 2.

FIG. 3 is a schematic diagram of operations performed by the collision avoidance system according to the present embodiment. In FIG. 3, the host vehicle 10 travels in the direction of the arrow Y1, and a following vehicle 100 travels in the direction of the arrow Y2.

In the host vehicle 10, the control device 30 activates the outward warning device 40, and the outward warning device 40 then performs the warning operation. The warning operation performed by the outward warning device 40 is at least one of a warning by lighting a lamp or displaying an image by the warning display unit 41, a warning by outputting a warning sound by the warning sound output unit 42, or a warning using the warning device in another vehicle through transmission of a warning signal from the warning signal transmission unit 43.

The warning by lighting a lamp or displaying an image by the warning display unit 41 appeals to the sense of sight of the driver of the following vehicle 100.

The warning by outputting a warning sound by the warning sound output unit 42 appeals to the sense of hearing of the driver of the following vehicle 100.

The warning signal transmitted from the warning signal transmission unit 43 is received by a warning signal reception unit 110 of the following vehicle 100. This operation enables a warning appealing to the sense of sight or hearing of the driver in the following vehicle 100.

Such warnings may be made to a vehicle traveling on the left or right side (including diagonally forward and backward areas) of the host vehicle 10 in addition to the following vehicle 100. The following vehicle 100 or the vehicle traveling on the left or right side (including diagonally forward and backward areas) of the host vehicle 10 may make a warning to another vehicle traveling further behind.

Figure 4:
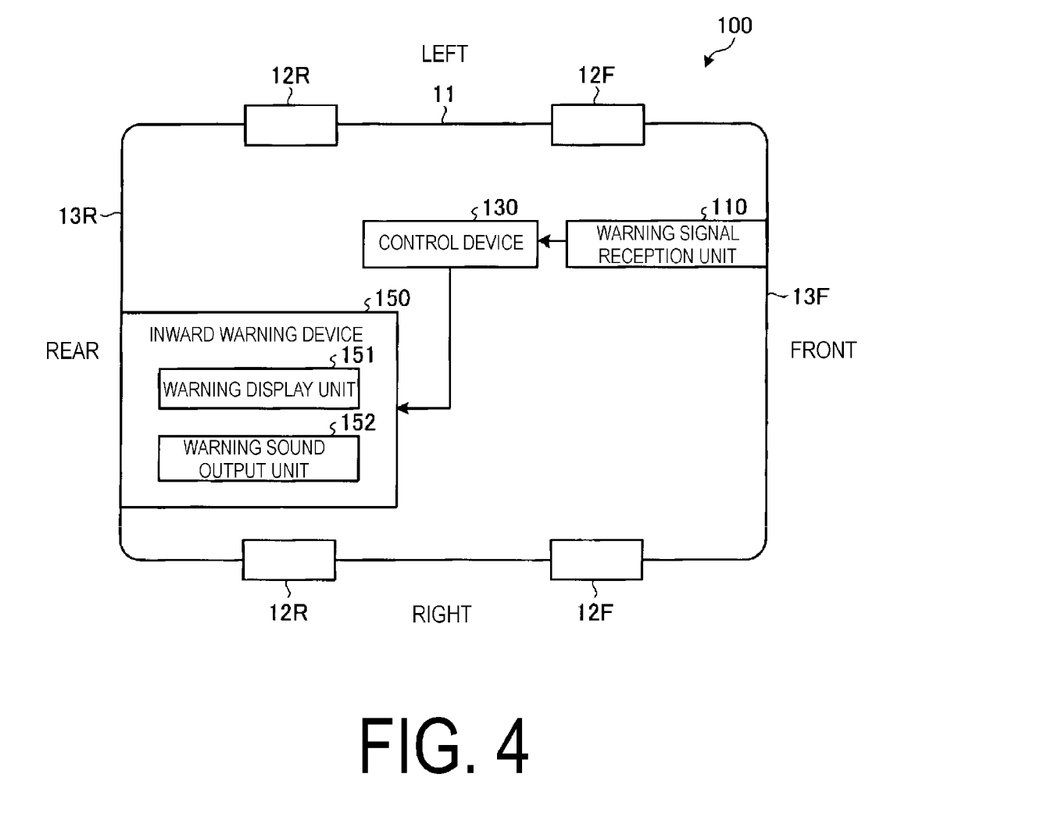
FIG. 4 is a schematic diagram of an example of another vehicle traveling in the vicinity of a host vehicle provided with the collision avoidance system according to the embodiment.

FIG. 4 is a schematic diagram of an example of another vehicle traveling in the vicinity of the host vehicle provided with the collision avoidance system according to the present embodiment. FIG. 4 illustrates an example in which the other vehicle is a following vehicle.

As illustrated in FIG. 4, the following vehicle 100 is a four-wheeled vehicle in the present embodiment. The following vehicle 100 has two front wheels 12F and two rear wheels 12R. The following vehicle 100 has a driver cab that a driver occupies. The following vehicle 100 includes a warning signal reception unit 110, a control device 130, and an inward warning device 150 that are disposed in a vehicle body 11. Note that the following vehicle 100 may be a vehicle other than four-wheeled vehicles.

The warning signal reception unit 110 is disposed in a front part 13F of the vehicle body 11 and receives the warning signal transmitted from the host vehicle 10 in FIG. 3. Upon receiving the warning signal, the warning signal reception unit 110 activates the control device 130.

The control device 130 activated by the warning signal reception unit 110 causes the inward warning device 150 to make a warning to the driver of the following vehicle 100.

The inward warning device 150 is disposed in a rear part 13R of the vehicle body 11 and includes a warning display unit 151 and a warning sound output unit 152. The warning display unit 151 makes a warning by lighting a lamp, displaying an image, or the like, to the driver of the following vehicle 100. The warning sound output unit 152 makes a warning by outputting a warning sound, to the driver of the following vehicle 100. The warning sound includes synthesized voice.

Operations of the collision avoidance system according to the present embodiment will now be described. The driver state detection unit 21 detects a state of the driver of the host vehicle 10. The driver state determination unit 31 determines whether the state of the driver detected by the driver state detection unit 21 is a drowsing state.

When the driver state determination unit 31 determines that the driver of the host vehicle 10 is in a drowsing state, the outward warning device control unit 32 activates the outward warning device 40. The outward warning device 40 makes a warning to the other vehicle. Then, the inward warning device control unit 33 activates the inward warning device 50. The inward warning device 50 makes a warning to the driver of the host vehicle. That is, after the outward warning device 40 makes a warning to the other vehicle, the inward warning device 50 makes a warning to the driver of the host vehicle.

These operations enable a warning to the other vehicle in the vicinity of the host vehicle and then a warning to the driver of the host vehicle on the basis of the state of the driver of the host vehicle, such as a drowsing state. When a warning is made to the driver first, the driver having awakened from the drowsing state may suddenly brake or turn the steering wheel. The operations described above enable a warning to the other vehicle and then a warning to the driver of the host vehicle. Thus, even when the driver who has received the warning from the inward warning device 50 awakens from the drowsing state and then suddenly brakes or turns the steering wheel, it can be expected that the driver of the other vehicle appropriately operates the brake or accelerator or turns the steering wheel because the outward warning device 40 makes a warning to the other vehicle before the warning to the host vehicle. This results in avoidance of a collision.

Second Embodiment

Figure 5:
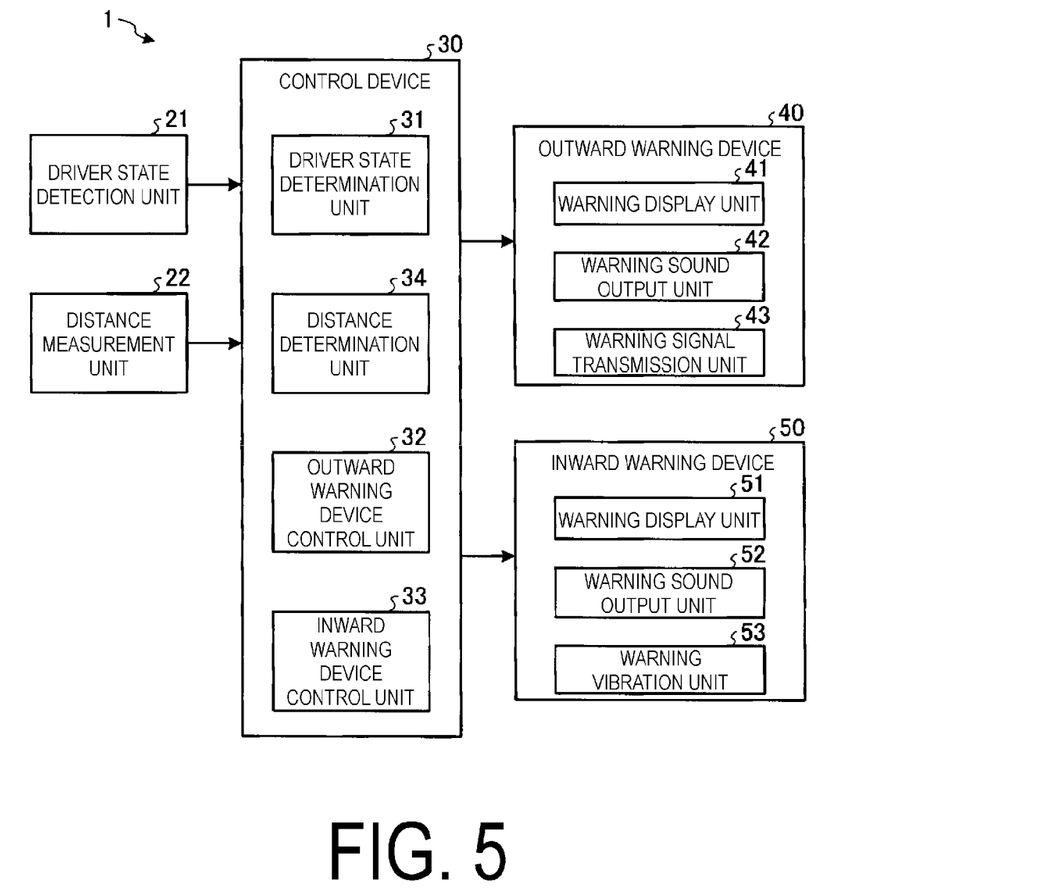
FIG. 5 is a function block diagram of a collision avoidance system according to a second embodiment.

FIG. 5 is a function block diagram of a collision avoidance system according to a second embodiment. The collision avoidance system 1 according to the present embodiment illustrated in FIG. 5 has the same configuration as that of the collision avoidance system according to the first embodiment described with reference to FIGS. 1 and 2 and further includes a distance measurement unit 22 and a distance determination unit 34.

The distance measurement unit 22 measures a distance between a vehicle (host vehicle) and another vehicle traveling in the vicinity of the host vehicle in a non-contact manner. The vehicle traveling in the vicinity of the host vehicle is, for example, one or both of a following vehicle traveling behind the host vehicle and a vehicle traveling on a side (left or right side) of the host vehicle. In addition to a vehicle traveling directly behind the host vehicle, the following vehicle for the measurement by the distance measurement unit 22 may be, for example, a vehicle traveling diagonally backward. The vehicle traveling on a side for the measurement by the distance measurement unit 22 may be, for example, a vehicle traveling diagonally forward. The distance measurement unit 22 performs the measurement at predetermined cycles (for example, every second).

The distance measurement unit 22 includes a radar device (a millimeter wave radar device, a Doppler radar device). The radar device can measure a distance between the host vehicle and the other vehicle by emitting radio waves (or ultrasonic waves) and then receiving radio waves (or ultrasonic waves) reflected by an object. Note that the distance measurement unit 22 may include at least one of a laser scanner or a three-dimensional range sensor. The distance measurement unit 22 may include an imaging device (a camera) capable of detecting an object in a non-contact manner by acquiring an optical image of the object. The distance measurement unit 22 including the imaging device may measure a distance on the basis of the acquired image. For example, the distance between the host vehicle and the other vehicle can be acquired on the basis of the size of the other vehicle in the acquired image. The distance measurement unit 22 performs the measurement at predetermined cycles (for example, every second).

The distance determination unit 34 determines whether the distance between the host vehicle and the other vehicle traveling in the vicinity of the host vehicle, measured by the distance measurement unit 22 is within a predetermined range (for example, within 20 m). When the distance between the host vehicle and the other vehicle measured by the distance measurement unit 22 is within the predetermined range (for example, within 20 m), the distance determination unit 34 activates the outward warning device control unit 32 and inward warning device control unit 33. The outward warning device control unit 32 causes the outward warning device 40 to make a warning, and the inward warning device control unit 33 causes the inward warning device 50 to make a warning.

When the distance between the host vehicle and the other vehicle measured by the distance measurement unit 22 is out of the predetermined range (for example, exceeds 20 m), the distance determination unit 34 does not activate either the outward warning device control unit 32 or inward warning device control unit 33. Thus, the inward warning device control unit 33 does not cause the inward warning device 50 to make a warning.

Figure 6:
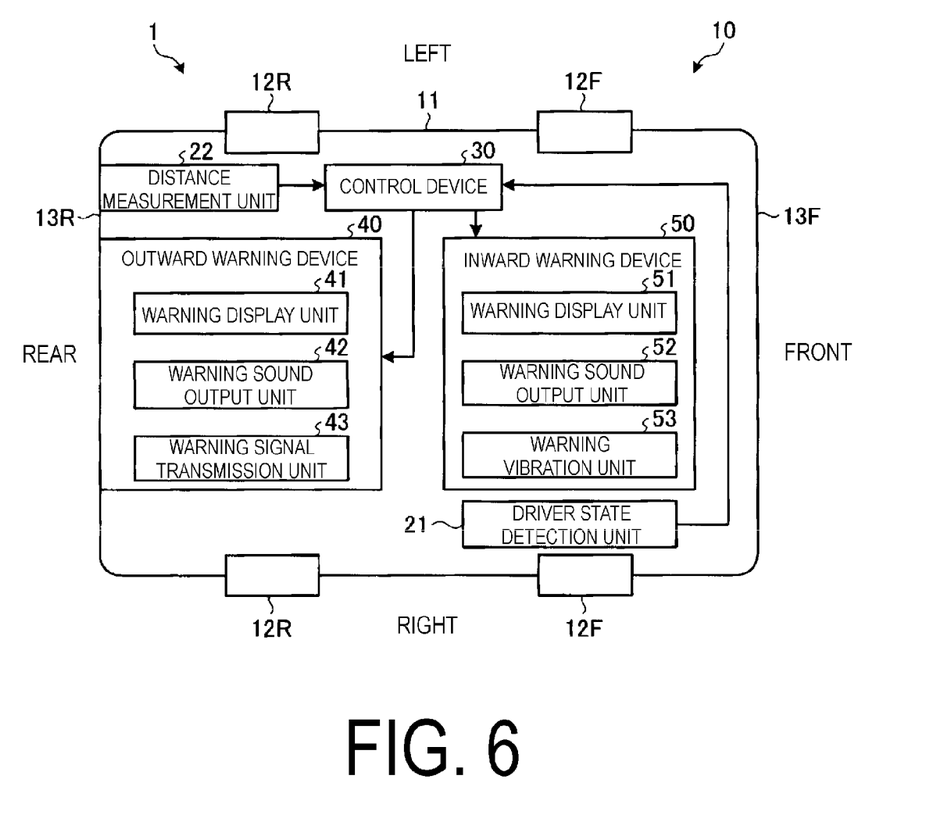
FIG. 6 is a schematic diagram of an example vehicle provided with the collision avoidance system according to the second embodiment.

FIG. 6 is a schematic diagram of an example vehicle provided with the collision avoidance system according to the present embodiment. As illustrated in FIG. 6, a vehicle body 11 according to the present embodiment has the same configuration as that described with reference to FIG. 2 and further includes the distance measurement unit 22. That is, a host vehicle 10 includes the distance measurement unit 22 disposed in a rear part 13R of the vehicle body 11. The distance measurement unit 22 can thus detect a distance from the host vehicle 10 to a following vehicle traveling behind the host vehicle 10 in a non-contact manner. In addition to a vehicle traveling directly behind the host vehicle, the distance measurement unit 22 may detect a distance to, for example, a vehicle traveling diagonally backward or on a side in a non-contact manner.

The other vehicle traveling in the vicinity of the host vehicle 10, such as a following vehicle, has the same configuration as that described above with reference to FIGS. 3 and 4.

Operations of the collision avoidance system according to the present embodiment will now be described. The driver state detection unit 21 detects a state of the driver of the host vehicle 10. The driver state determination unit 31 determines whether the state of the driver detected by the driver state detection unit 21 is a drowsing state.

When the driver state determination unit 31 determines that the driver of the host vehicle 10 is in a drowsing state, the distance determination unit 34 determines whether the distance between the host vehicle and another vehicle traveling in the vicinity of the host vehicle, measured by the distance measurement unit 22 is within a predetermined range.

When the distance determination unit 34 determines that the distance between the host vehicle and the other vehicle traveling in the vicinity of the host vehicle is within the predetermined range, the outward warning device control unit 32 activates the outward warning device 40. The outward warning device 40 makes a warning to the other vehicle. Then, the inward warning device control unit 33 activates the inward warning device 50. The inward warning device 50 makes a warning to the driver of the host vehicle. That is, after the outward warning device 40 makes a warning to the other vehicle, the inward warning device 50 makes a warning to the driver of the host vehicle.

In contrast, when the distance determination unit 34 determines that the distance between the host vehicle and the other vehicle traveling in the vicinity of the host vehicle is out of the predetermined range (exceeds the predetermined range), the outward warning device control unit 32 and inward warning device control unit 33 do not activate the outward warning device 40 and inward warning device 50, respectively. Thus, the outward warning device 40 and inward warning device 50 do not make a warning.

When a determination is made that the host vehicle being operated by a driver in a drowsy state and the distance between the host vehicle and the other vehicle traveling in the vicinity of the host vehicle is within the predetermined range, these operations enable a warning to the other vehicle and then a warning to the driver of the host vehicle. Thus, even when the driver who has received the warning from the inward warning device 50 awakens from the drowsing state and then suddenly brakes or turns the steering wheel, it can be expected that the driver of the other vehicle appropriately operates the brake or accelerator or turns the steering wheel because the outward warning device 40 makes a warning to the other vehicle, such as a following vehicle, before the warning to the host vehicle. This results in avoidance of a collision.

With the collision avoidance system according to the second embodiment, differing from the first embodiment, when the distance between the host vehicle and the other vehicle exceeds the predetermined range, it is assumed that a collision hardly occurs, which eliminates the need to make a warning and thus prevents the outward warning device 40 and inward warning device 50 from making a warning. Thus, an ineffective warning can be prevented.

Third Embodiment

Figure 7:
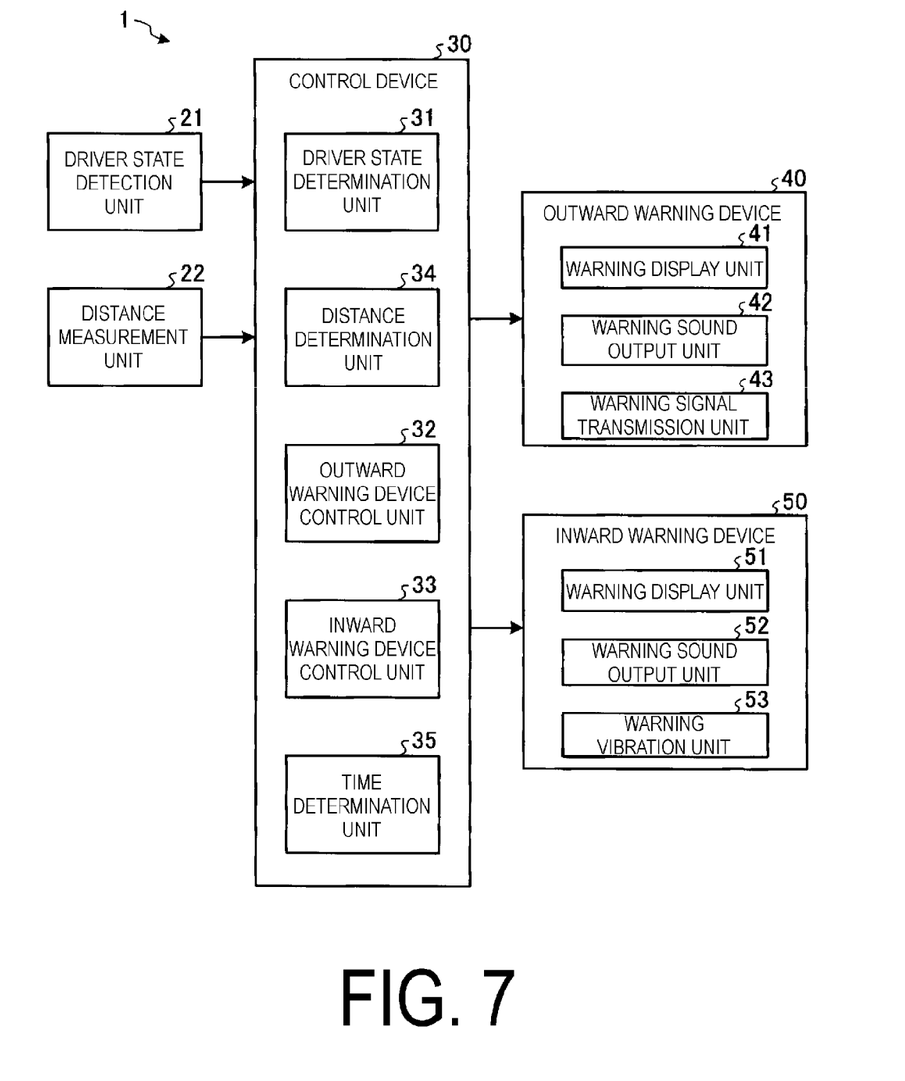
FIG. 7 is a function block diagram of a collision avoidance system according to a third embodiment.

FIG. 7 is a function block diagram of a collision avoidance system according to a third embodiment. The collision avoidance system 1 according to the present embodiment illustrated in FIG. 7 has the same configuration as that of the collision avoidance system according to the second embodiment described with reference to FIGS. 5 and 6 and further includes a time determination unit 35.

The time determination unit 35 determines the time elapsed since a warning is made to the other vehicle by the outward warning device 40. When a predetermined time (for example, one second) has elapsed since the warning to the other vehicle by the outward warning device 40, the control unit 32 activates the inward warning device 50 to make a warning to the driver of the host vehicle.

The predetermined time may be set preliminarily or may be set by the driver. The predetermined time may be adjusted depending on the travel speed of the host vehicle. It is desirable that the predetermined time be shorter as the host vehicle travels faster and longer as the host vehicle travels slower.

In the present embodiment, the control device 30 includes the time determination unit 35, and a vehicle body 11 has the same configuration as that described above with reference to FIG. 6. The other vehicle traveling in the vicinity of the host vehicle 10, such as a following vehicle, has the same configuration as that described above with reference to FIGS. 3 and 4.

Operations of the collision avoidance system according to the present embodiment will now be described. The driver state detection unit 21 detects a state of the driver of the host vehicle 10. The driver state determination unit 31 determines whether the state of the driver detected by the driver state detection unit 21 is a drowsing state.

When the driver state determination unit 31 determines that the driver of the host vehicle 10 is in a drowsing state, the distance determination unit 34 determines whether the distance between the host vehicle and another vehicle traveling in the vicinity of the host vehicle, measured by the distance measurement unit 22 is within a predetermined range.

When the distance determination unit 34 determines that the distance between the host vehicle and the other vehicle traveling in the vicinity of the host vehicle is within the predetermined range, the outward warning device control unit 32 activates the outward warning device 40. The outward warning device 40 makes a warning to the other vehicle. Then, when the time determination unit 35 determines that a predetermined time has elapsed, the inward warning device control unit 33 activates the inward warning device 50. The inward warning device 50 makes a warning to the driver of the host vehicle. That is, after the elapse of the predetermined time since the outward warning device 40 makes a warning to the other vehicle, the inward warning device 50 makes a warning to the driver of the host vehicle.

In contrast, when the distance determination unit 34 determines that the distance between the host vehicle and the other vehicle traveling in the vicinity of the host vehicle is out of the predetermined range (exceeds the predetermined range), the outward warning device control unit 32 and inward warning device control unit 33 do not activate the outward warning device 40 and inward warning device 50, respectively. Thus, the outward warning device 40 and inward warning device 50 do not make a warning.

The collision avoidance system according to the third embodiment, differing from the first embodiment, considers that a collision hardly occurs in the case where the distance between the host vehicle and the other vehicle exceeds the predetermined range. Since a warning is not required in this case, the outward warning device 40 and inward warning device 50 do not make a warning. Thus, an ineffective warning can be prevented.

The collision avoidance system according to the third embodiment, differing from the second embodiment, sufficiently ensures the time from when the outward warning device 40 makes a warning to the other vehicle until when the inward warning device 50 makes a warning to the driver of the host vehicle. This indicates that the time for the driver of the other vehicle to appropriately operate the brake or accelerator or turn the steering wheel can be sufficiently ensured, resulting in avoidance of a collision.

Modified examples of the collision avoidance system according to the present embodiment will now be described.

First Modified Example

The driver state detection unit 21 and driver state determination unit 31 may respectively detect and determine the time elapsed from the starting time of driving. For example, when the host vehicle 10 is a rented vehicle, the driver may not be accustomed to driving the host vehicle 10 immediately after the start of driving (when the time elapsed from the starting time of driving is short). In this case, making a warning to the other vehicle sufficiently ensures the time for the driver of the other vehicle to appropriately operate the brake or accelerator or turn the steering wheel, resulting in avoidance of a collision.

Second Modified Example

A warning to the other vehicle may be made depending on the attribute of the driver. For example, the driver may preliminarily input the driving experience, color of the driver's license (for example, gold or the other colors), and type of the driver's license (for example, whether the driver has a license for large vehicles), to adjust the predetermined time to be determined by the time determination unit 35.

Third Modified Example

A warning to the other vehicle may be made when a mobile phone or smartphone of the driver has an incoming call during driving. Even when the driver reacts to (is surprised with) sounding of a ringtone and then suddenly brakes or turns the steering wheel, it can be expected that the driver of the other vehicle appropriately operates the brake or accelerator or turns the steering wheel, because the outward warning device 40 makes a warning to the other vehicle and then the inward warning device 50 makes a warning to the driver of the host vehicle 10. This results in avoidance of a collision. A ringtone can be detected with a microphone provided in the vehicle.

Fourth Modified Example

The driver state detection unit 21 and driver state determination unit 31 may respectively detect and determine another state of the driver in addition to a drowsing state. For example, a state of the driver looking aside while driving or a state of a fit of a chronic disease of the driver (for example, epilepsy) may be detected, and the outward warning device 40 may make a warning to the other vehicle and then the inward warning device 50 may make a warning to the driver of the host vehicle 10. The state of the driver looking aside while driving can be detected through an analysis of a captured image of the driver's face. The fit of a chronic disease of the driver can be detected with, for example, an electromyogram.

Collision Avoidance Method

Figure 8:
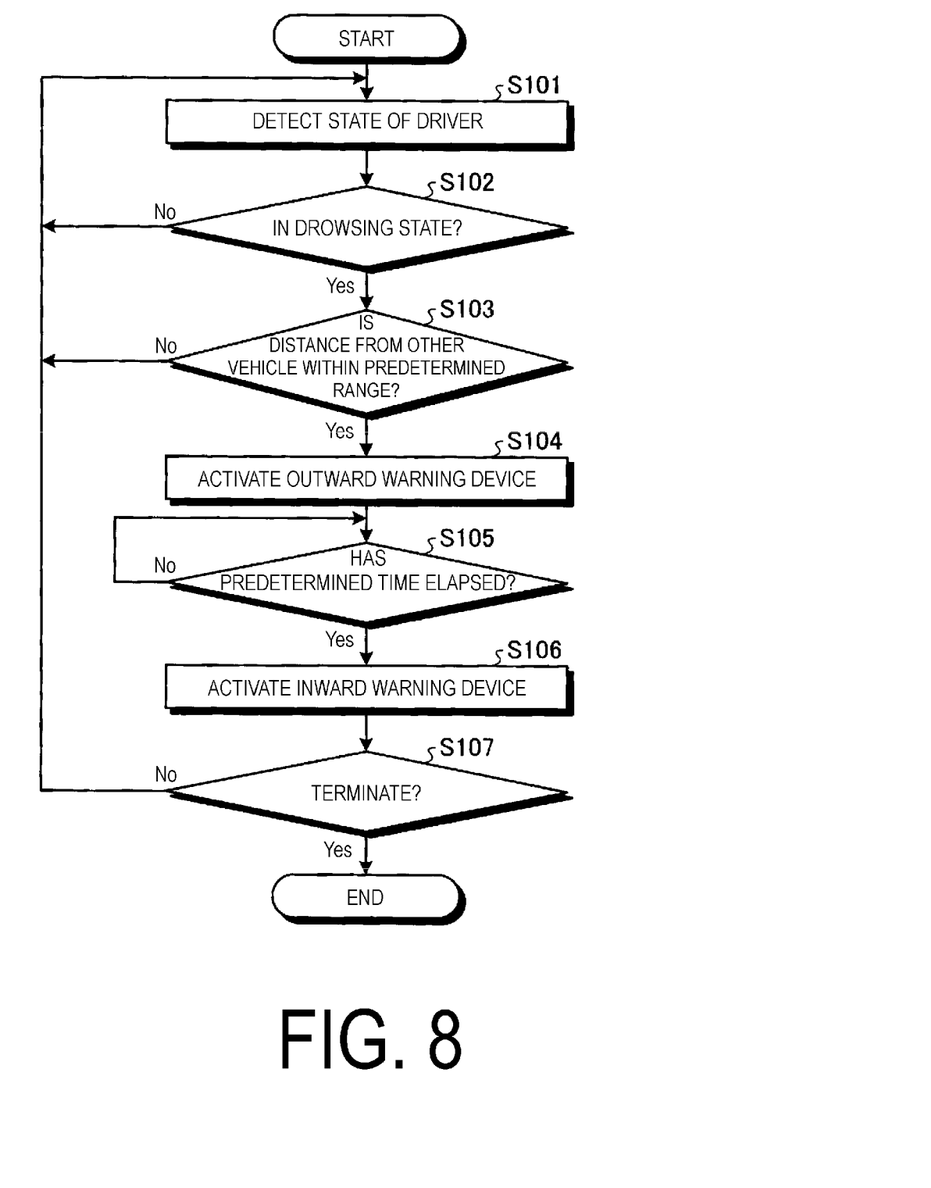
FIG. 8 is a flowchart illustrating an example of a collision avoidance method carried out by the collision avoidance system according to the embodiments.

FIG. 8 is a flowchart illustrating an example of a collision avoidance method carried out by the collision avoidance system according to the present embodiment. As illustrated in FIG. 8, the driver state detection unit 21 detects a state of the driver of the host vehicle 10 (Step S101). The driver state determination unit 31 determines whether the state of the driver detected by the driver state detection unit 21 is a drowsing state (Step S102).

When the driver state determination unit 31 determines that the driver of the host vehicle 10 is in a drowsing state (Yes in Step S102), the distance determination unit 34 determines whether the distance between the host vehicle and another vehicle traveling in the vicinity of the host vehicle, measured by the distance measurement unit 22 is within a predetermined range (Step S103).

When the distance determination unit 34 determines that the distance between the host vehicle and the other vehicle traveling in the vicinity of the host vehicle is within the predetermined range (Yes in Step S103), the outward warning device control unit 32 activates the outward warning device 40 to make a warning (Step S104).

Thereafter, the time determination unit 35 determines whether a predetermined time has elapsed (Step S105). When the time determination unit 35 determines that the predetermined time has elapsed (Yes in Step S105), the inward warning device control unit 33 activates the inward warning device 50 to make a warning (Step S106).

Thereafter, a determination is made as to whether the procedure of this system terminates (Step S107). When it is determined that the procedure of the system terminates (Yes in Step S107), the procedure of the system terminates. When it is determined that the procedure of the system does not terminate (No in Step S107), the procedure of the system continues.

When the driver state determination unit 31 determines that the driver of the host vehicle 10 is not in a drowsing state in Step S102 (No in Step S102) or when the distance determination unit 34 determines that the distance between the host vehicle and the other vehicle traveling in the vicinity of the host vehicle is out of the predetermined range in Step S103 (No in Step S103), the procedure of the system goes back to Step S101 and continues.

When the time determination unit 35 determines that the predetermined time has not elapsed in Step S105 (No in Step S105), the procedure goes back to Step S105 and the time determination unit 35 continues determination.

The processes in Steps S103, S105 may be omitted. In the case of omitting the processes in Steps S103, S105 (which corresponds to the first embodiment), when the driver state determination unit 31 determines that the driver of the host vehicle 10 is in a drowsing state (Yes in Step S102), the outward warning device control unit 32 activates the outward warning device 40 to make a warning (Step S104), and then the inward warning device control unit 33 activates the inward warning device 50 to make a warning (Step S106), regardless of the distance between the host vehicle and the other vehicle traveling in the vicinity of the host vehicle.

In the case of performing the process in Step S103 and omitting the process in Step S105 (which corresponds to the second embodiment), when the driver state determination unit 31 determines that the driver of the host vehicle 10 is in a drowsing state (Yes in Step S102) and when the distance determination unit 34 determines that the distance between the host vehicle and the other vehicle traveling in the vicinity of the host vehicle is within the predetermined range (Yes in Step S103), the outward warning device control unit 32 activates the outward warning device 40 to make a warning (Step S104), and then the inward warning device control unit 33 activates the inward warning device 50 to make a warning (Step S106).

The invention claimed is:

1. A collision avoidance system comprising:
   a driver state detection unit configured to detect a state of a driver of a host vehicle;
   an outward warning device configured to perform an outward warning operation pertaining to a warning directed at another vehicle traveling in a vicinity of the host vehicle;
   an inward warning device configured to perform an inward warning operation pertaining to a warning directed at the driver of the host vehicle; and
   a control unit configured to control the outward warning device and the inward warning device on the basis of the state of the driver detected by the driver state detection unit,
   the control unit being configured to cause the outward warning device and the inward warning device respectively to perform the outward warning operation and then the inward warning operation on the basis of the state of the driver.

2. The collision avoidance system according to claim 1, further comprising a distance measurement unit configured to measure a distance between the host vehicle and the other vehicle,
   upon the distance measured by the distance measurement unit being within a predetermined range, the control unit being configured to cause the outward warning device and the inward warning device to perform the outward warning operation and the inward warning operation.

3. The collision avoidance system according to claim 1, wherein the other vehicle includes a following vehicle traveling behind the host vehicle.

4. The collision avoidance system according to claim 1, wherein the driver state detection unit is configured to detect a drowsing state of the driver.

5. The collision avoidance system according to claim 4, wherein the driver state detection unit includes a brainwave sensor configured to detect brainwaves of the driver and is configured to detect the drowsing state of the driver on the basis of the brainwaves of the driver.

6. The collision avoidance system according to claim 4, wherein the driver state detection unit includes an imaging unit configured to detect an image of the driver and is configured to detect the drowsing state of the driver on the basis of the image of the driver.

7. The collision avoidance system according to claim 1, wherein the control unit is configured to cause the outward warning device to perform the outward warning operation and then, after a predetermined time elapses, cause the inward warning device to perform the inward warning operation.

8. The collision avoidance system according to claim 1, wherein the outward warning operation includes at least one of displaying a predetermined display directed at the other vehicle or emitting a predetermined sound toward the other vehicle.

9. The collision avoidance system according to claim 1, wherein the outward warning operation includes transmitting a signal to the other vehicle for activating another warning device provided in the other vehicle.

10. A collision avoidance method comprising the steps of:
    detecting a state of a driver of a host vehicle;
    performing an outward warning operation pertaining to a warning directed at another vehicle traveling in a vicinity of the host vehicle; and
    performing an inward warning operation pertaining to a warning directed at the driver of the host vehicle,
    the outward warning operation being performed and then the inward warning operation being performed on the basis of the state of the driver.

11. The collision avoidance method according to claim 10, further comprising:
    measuring a distance between the host vehicle and the other vehicle, and
    causing the outward warning device and the inward warning device to perform the outward warning operation and the inward warning operation when the distance measured is within a predetermined range.

12. The collision avoidance method according to claim 10, wherein detecting the state of the driver further comprises detecting a drowsing state of the driver.

13. The collision avoidance method according to claim 12, further comprising detecting brainwaves of the driver, wherein detecting the drowsing state of the driver is based on the brainwaves of the driver.

14. The collision avoidance method according to claim 12, further comprising detecting an image of the driver, wherein detecting the drowsing state of the driver is based on the image of the driver.

15. The collision avoidance method according to claim 10, further comprising performing the outward warning operation and then, after a predetermined time elapses, performing the inward warning operation.

16. The collision avoidance method according to claim 10, wherein performing the outward warning operation includes displaying a predetermined display directed at the other vehicle or emitting a predetermined sound toward the other vehicle.

17. The collision avoidance method according to claim 10, wherein performing the outward warning operation includes transmitting a signal to the other vehicle for activating another warning device provided in the other vehicle.

* * * * *